United States Patent
Sklandnev et al.

[11] Patent Number: 5,855,551
[45] Date of Patent: Jan. 5, 1999

[54] INTEGRAL SHEATHING APPARATUS FOR TISSUE RECOGNITION PROBES

[75] Inventors: Victor N. Sklandnev, Vaucluse; Richard L. Thompson, Killarney Heights, both of Australia; Irwin Wunderman, Mtn. Vica, Calif.

[73] Assignee: Polartechnics Limited, Sydney, Australia

[21] Appl. No.: 818,910

[22] Filed: Mar. 17, 1997

[51] Int. Cl.$^6$ .................................................. A61B 5/00
[52] U.S. Cl. .......................................... 600/372; 600/310
[58] Field of Search .................................. 600/304, 310, 600/313, 325, 327, 331, 337, 333, 341, 351, 373, 376, 478; 128/849, 918; 607/138, 116, 11

[56] References Cited

U.S. PATENT DOCUMENTS

| | | | |
|---|---|---|---|
| 3,647,299 | 3/1972 | Lavallee | 356/41 |
| 3,910,701 | 10/1975 | Henderson et al. | 356/39 |
| 3,994,590 | 11/1976 | Di Martini et al. | 356/178 |
| 4,587,421 | 5/1986 | Robertson | 250/239 |
| 4,942,877 | 7/1990 | Sakai et al. | 128/633 |
| 5,036,853 | 8/1991 | Jeffcoat et al. | 128/634 |
| 5,234,835 | 8/1993 | Nestor et al. | 600/331 |
| 5,242,390 | 9/1993 | Goldrath | 600/135 |
| 5,411,024 | 5/1995 | Thomas et al. | 128/634 |
| 5,427,093 | 6/1995 | Ogawa et al. | 128/633 |
| 5,520,177 | 5/1996 | Ogawa et al. . | |
| 5,562,717 | 10/1996 | Tippey et al. | 607/138 |
| 5,634,459 | 6/1997 | Gardosi | 600/376 |

OTHER PUBLICATIONS

Mendelson, Ph.D. et al., Design and Evaluation of a New Reflectance Pulse Oximeter Sensor, Medical Instrument, vol. 11, No. 4, pp. 187–173, 1988.

Neuman, M.R., In Medical Instrumentation: Application and Design, pp. 265–266, Webster, J.G. (ed) 2nd Ed. Boston: Houghton Miffliin, 1992.

*Primary Examiner*—Danton D. DeMille
*Assistant Examiner*—David M. Ruddy
*Attorney, Agent, or Firm*—Gottlieb, Rackman & Reisman, P.C.

[57] ABSTRACT

The invention incorporates an opto-electronic section in the tip of the sheath cover for a diagnostic probe that makes both electric and optical measurements of tissue contacted by the sheath. In addition the invention provides a piece of turbid material such as a polymer of controlled composition as a built-in calibrator attached to the outside of the tip of the sheath. In one embodiment the probe sheath in fabricated from a flexible material which can be rolled up prior to fitting and when fitted to the tip of the probe can be rolled down the shaft of the probe for use and then rolled back off the shaft for disposal.

8 Claims, 2 Drawing Sheets

INTEGRAL SHEATHING APPARATUS FOR TISSUE RECOGNITION PROBES

FIELD OF THE INVENTION

This invention is a sheath intended for the recognition of tissue types and in particular for the detection of cervical precancer and cancer for use with a probe that performs both optical and electrical measurements while it is scanned over the surface of tissue, e.g. the cervix, and from these measurements makes a diagnosis of the health of the tissue.

BACKGROUND OF THE INVENTION

The medical profession often needs to have an objective assessment of the health of the tissue of a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient.

It is well known, for example, that early detection of tissues displaying pre-cancer or cancer modifications is important for successful medical treatment. We have already disclosed an apparatus and method for carrying out this detection in patent application Ser. No. 08/332,830, assigned to the same assignee as the current invention.

Between uses probes can be disinfected by soaking in a suitable solution. For many patients this procedure is not acceptable. They require that the probe has not previously been used on other patients for fear of cross-contamination and infection. This requirement can be achieved by equipping the probe with a discardable, sterile sheath. Such an assembly must ensure that no part of the probe which is used on a patient could have come in contact with a previous patient. Sheaths that have been designed for other types of probes lack features that would make them suitable for use on a probe that performs both optical and electrical measurements while it is scanned over the surface of the cervix. For example ultrasonic probe sheaths would not be suitable. In particular they do not have provision to make simultaneous optical and electrical measurements. The particular difficulties that have been overcome by this invention arise from the fact that the both electrical and optical measurements are to be performed on the same area of tissue. It is therefore not feasible to install a simple sheath such as a condom over the tip of the probe. Such a sheath may, for example, enable some optical measurements to be made but would prevent electrical contact being made with the tissue with the optically transparent cover in place.

SUMMARY OF THE INVENTION

This difficulty is overcome in the present invention by incorporating electrodes in the tip of the sheath. However this is accomplished in such a manner that the sheath does not have to match the detection components of a pre-existing probe as was disclosed in our copending application filed this date entitled "Sheathed Probes For Tissue Type Recognition" Ser. No. 08/818,912.

The present invention sites the opto-electronics components at the working face of the sheath in a high density array. This is achieved by employing bare opto-electronic dice rather than packaged components and mounting these in close proximity to each other in an optically designed chamber.

Close spacing of opto-electronics components is customarily avoided because of the difficulties of providing adequate electrical and optical isolation. Optical fibers are often used to enable the opto-electronics components to be held remote from each other, from the working face of the probe and from the patient to achieve the required isolations. This invention overcomes these isolation problems while achieving the needed high resolution of measurement and small enough size to fit at the tip of a sheath.

In addition the invention provides a built-in calibrator. This is achieved by attaching to the outside of the tip of the sheath a piece of turbid material such as a polymer of controlled composition. This material acts in the manner of the tissue to be measured in that it backscatters the light from the probe tip to a controlled degree. This enables the probe's computer to check the overall performance of the optical system thereby verifying that the probe and its sheath are performing optically according to specifications and that the sheath has been correctly fitted. The piece of turbid material is removed prior to using the probe on a patient.

DETAILED DESCRIPTION OF PREFERRED EMBODIMENTS

The sheath of the present invention does not hinder the reading of the optical and electrical properties of the tissue being determined at effectively the same place.

The optical system for the sheath employs hybrid opto-electronic systems that place the opto-electronics components at the tip of the sheath.

A detailed description of useful hybrid opto-electronics elements is contained in our copending application filed this same date entitled "Hybrid Probe For Tissue Type Recognition" Ser. No. 08/818,912, which is included herein by reference. As explained in that application, a hybrid probe is primarily distinguished by the avoidance of the use of optical fibers to convey illumination to and/or from the active portion of the probe. It is designed to examine areas of tissue having a diameter of the order of 2 mm, which requires that photodiode detectors be placed in close juxtaposition with light emitters yet optically isolated so that light signals do not pass directly from an emitter to a detector without intervention (i.e. backscattering) by the tissue under examination. This is accomplished in the hybrid probe by the use of metal barriers. The metal barriers also shield the detector circuitry from electrical interference carried by current pulses that must be applied to the LEDs to induce them to emit light to illuminate the portion of the tissue being tested. The metal barrier may be left floating or grounded, but can also serve an additional role as an electrode for making electrical measurements to replace or supplement the two or three noble metal electrodes adjacent to the hybrid circuit normally used for the electrical measurements to be made on the tissue.

In addition the hybrid structure has a preamplifier in close proximity to the photodiodes to amplify the small current from the photodiode detectors and feed it to the electronics in the handle of the probe and from there to the analysis circuitry.

It is not economical to employ optical fibers in a disposable sheath because the quality of optical coupling that is required for precise optical measurements is costly to achieve. The radiation output of LEDs is temperature sensitive but for precise measurements can be compensated by using a characteristic of the LED to determine its own temperature. The bandgap potential of LEDs is a known function of temperature, allowing the temperature to be determined by applying a known current to the diode and measuring the potential across it. This can then be used to correct for the output of the LED using established equations thereby compensating for the changed radiation emission caused by temperature changes. Further details are provided in the accompanying application mentioned above.

Figure 1:
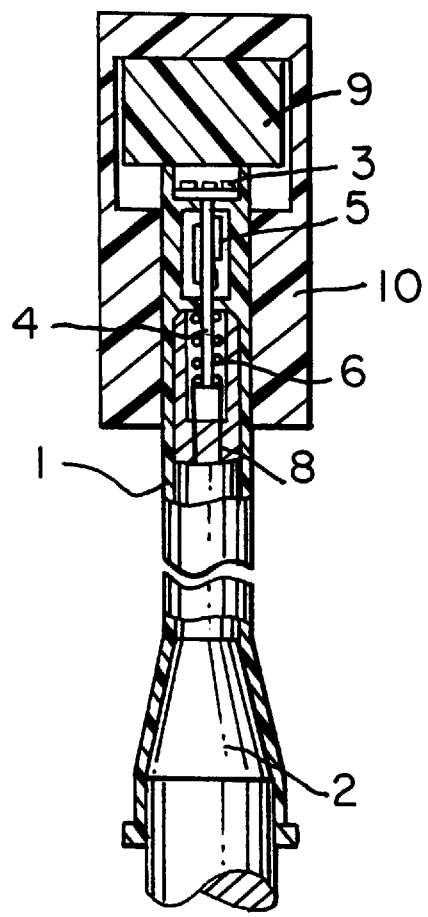
FIG. 1 is an illustration of the sheath fitted to a probe shaft.
Figure 2:
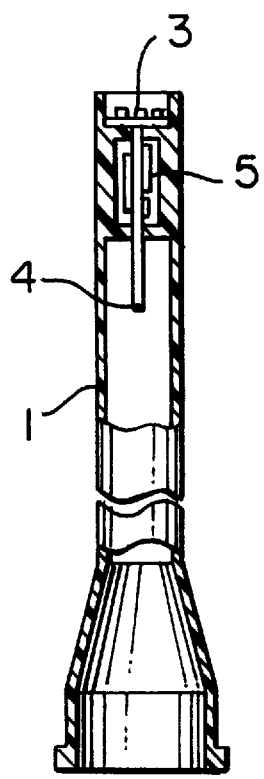
FIG. 2 shows the sheath alone without the probe or calibrator.

FIG. 1 shows the sheath 1 of this invention as it appears when fitted to a probe 2. At the tip of the sheath is mounted the opto-electronics section 3 which includes a light emitter, an electrode and a photodiode detector for electrical measurement on the tissue. A circuit board 4 carries electronic components 5 needed to operate the opto-electronics and electrodes. The rear end of the circuit board 4 mates with spring contacts 6 that provide the necessary electrical connections to the tip circuits. Wires 8 connect the contacts to the circuits in the handle of the probe 2.

The method of making the electrical connections from the tip of the sheath 1 to the probe 2 via the board 4 and contacts 6 is by way of example only. Other methods such as by using a plug and socket are possible and would be employed under appropriate circumstances.

Probes for the detection of tissue abnormalities need to be able to resolve small areas of tissue so the tip of the sheath should in general not be greater than 10 mm in diameter. A preferred size is nearer to 5 mm. It is usually not necessary to detect abnormalities with dimension below 3 mm so sheaths of this diameter would rarely be needed.

Because there is only one orientation of the sheath that will ensure that the circuits board 4 mates with spring contacts 6, the cross section of the body of the probe and of the sheath need to be other than circularly symmetrical. The provision of a groove in the body of the probe and a corresponding key in the sheath will ensure that this requirement is met. The groove can also serve the purpose of allowing trapped air to escape as the sheath is fitted.

Elastomer calibrators may be assembled on the tip with the other components of the sheath and is removed after calibrating the system and before the probe put into use.

Another form of calibrator comprises a turbid elastomer on top of which is placed a film of flexible polymer which is intended to simulate the structure of the material that is to be measured. The latter may for example be a layer of precancerous cells on cervical tissue. The layer of polymer film that is placed over the elastomer should have optical characteristics analogous to the material to be detected by the probe. In the case of cervical intra-epithelial neoplasia, the cervical tissue becomes covered with a layer of abnormal cells. A calibrator intended to check the performance of a device that is to detect this layer of cells may provide more reliable diagnoses if it is calibrated in an environment equivalent to that pertaining during the diagnostic probing, that is, by using a layered calibrator.

A calibrator 9 mounted in a holder 10 is fitted to the tip of the assembly. The holder 10 and calibrator are removed from the sheath 1 immediately prior to use on the patient.

An important feature of the invention is the fact that the electrodes are an integral part of the tip section and are not an addition in the form of a separately molded section. Problems of sealing the electrodes are thus avoided. The tip section is a robust, single piece so that the danger of leaks and consequent cross-contamination are obviated. There is no need for thin optical widows and no optical coupling liquids are needed to ensure reliable optical readings.

In use, the sheath 1 would be supplied in a sealed package to ensure that it was sterile and the package would be opened only immediately prior to use. At that point, the sheath 1 would be slid over the probe shaft 2 and its handle and then slipped out of its package. Calibration by the controller must be requested by the operator since the unit will not operate unless recently calibrated. The calibrator 9 and its holder 10 are then removed and the probe is employed on the patient. After use the package is slid back over the sheath and used to remove and to discard it as a contaminated item. The calibrator is not reused so that source of potential contamination is avoided.

In another embodiment the tubular section of the sheath 1 is fabricated from a flexible material which can be rolled up in the manner of a condom. The shaft of the probe 2 is inserted into the tip of the sheath and mated with the circuit board 4. The tubular section of the sheath is then rolled down the shaft of the probe 2 until it reaches the handle. The system is then used in the manner described above for the other embodiment. At the conclusion of use of the system, the tubular section of the sheath is rolled back over the tip to provide a cover for the contaminated section of the sheath prior to disposal. This embodiment has the advantage of simplicity and safety when it comes to being discarded.

Although the invention has been described in terms of preferred embodiments its full scope is not so limited. Accordingly the invention is defined by the proper legal scope of the following claims.

What is claimed is:

1. A sheath for a medical probe which can be removed from the probe and replaced with another identical sheath to prevent cross contamination between patients comprising
   an opto-electronic section fitted with at least one electrode and at least one light emitter and photodiode detector at the tip of a sheath for providing and detecting electrical and optical signals simultaneously and a circuit for transmitting electrical signals representative of the detected electrical and optical signals to the probe as it moves across an area of tissue.

2. The sheath of claim 1 wherein said sheath tip has a diameter between 3 mm and 10 mm.

3. The sheath as claimed in claim 1 that is fitted with a piece of turbid material at the tip which serves the purpose of checking the calibration of the combined sheath and probe and which can be removed prior to using the probe on a patient.

4. A sheath as claimed in claim 1 fabricated from a flexible material which can be rolled up prior to fitting on a probe having a shaft and when fitted to the tip of the probe can be rolled down the shaft of the probe for use and then rolled back off the shaft for disposal.

5. A medical probe and a sheath which can be removed from the probe and replaced with another identical sheath to prevent cross contamination between patients said sheath comprising
   an opto-electronic section fitted with at least one electrode and at least one light emitter and photodiode detector at the tip of said sheath for providing and detecting electrical and optical signals simultaneously and a circuit for transmitting electrical signals representative of the detected electrical and optical signals to the probe as it moves across an area of tissue.

6. The medical probe and sheath of claim 5 wherein said sheath tip has a diameter between 3 mm and 10 mm.

7. The medical probe and sheath as claimed in claim 5 wherein said sheath is fitted with a piece of turbid material at the tip which serves the purpose of checking the calibration of the combined probe and sheath and which can be removed prior to using the probe and sheath on a patient.

8. A medical probe and sheath as claimed in claim 5, said probe having a shaft, and said sheath fabricated from a flexible material which can be rolled up prior to fitting on the probe and when fitted to the tip of the probe can be rolled down the shaft of the probe for use and then rolled back off the shaft for disposal.

\* \* \* \* \*